(12) United States Patent
Murray

(10) Patent No.: US 6,680,479 B1
(45) Date of Patent: Jan. 20, 2004

(54) METHOD AND APPARATUS TO DETECT THE PRESENCE OF WATER ON A SURFACE

(75) Inventor: Stuart Charles Murray, West Bridgford (GB)

(73) Assignee: Lattice Intellectual Property Limited, London (GB)

( * ) Notice: Subject to any disclaimer, the term of this patent is extended or adjusted under 35 U.S.C. 154(b) by 0 days.

(21) Appl. No.: 09/601,325

(22) PCT Filed: Jan. 19, 1999

(86) PCT No.: PCT/GB99/00165

§ 371 (c)(1), (2), (4) Date: Sep. 25, 2000

(87) PCT Pub. No.: WO99/40412

PCT Pub. Date: Aug. 12, 1999

(30) Foreign Application Priority Data

Feb. 6, 1998 (GB) .............................................. 9802473

(51) Int. Cl.⁷ .......................... G01N 21/31; G01N 21/88
(52) U.S. Cl. .............................. 250/339.1; 250/339.01; 250/339.11; 250/339.12; 250/341.8
(58) Field of Search ........................ 250/339.01, 339.11, 250/339.12, 341.8, 339.1

(56) References Cited

U.S. PATENT DOCUMENTS

| | | | |
|---|---|---|---|
| 3,885,091 A | | 5/1975 | Harold et al. |
| 4,274,091 A | * | 6/1981 | Decker .................. 250/339.11 |
| 4,465,929 A | * | 8/1984 | Edgar ...................... 250/252.1 |
| 4,913,558 A | * | 4/1990 | Wettervik et al. ............... 374/4 |
| 6,102,617 A | * | 8/2000 | Hampton ...................... 405/52 |
| 6,271,878 B1 | * | 8/2001 | Sera ........................... 348/164 |

FOREIGN PATENT DOCUMENTS

| | | |
|---|---|---|
| GB | 2 008 745 A | 6/1979 |
| JP | 03 115838 | 8/1991 |
| WO | WO 98 22806 A | 5/1998 |

* cited by examiner

*Primary Examiner*—Constantine Hannaher
*Assistant Examiner*—Shun Lee
(74) *Attorney, Agent, or Firm*—Oblon, Spivak, McClelland, Maier & Neustadt, P.C.

(57) ABSTRACT

A water detecting apparatus includes a source of infra-red radiation which is reflected off an inner surface of a pipe wall onto a mirror directing the infra-red signal along a path to an infra-red detector connected by an electrical signal path to an electronic control. The path is interrupted by a rotating chopper having windows occupied by two optical filters. The first optical filter only passes an infra-red signal of wavelength 1900 nm which is absorbed by water, while the second optical filter only passes an infra-red signal of wavelength 2200 nm, another wavelength absorbed by water, but not to the same extent as the 1900 nm wavelength. The 2200 nm wavelength serves as a reference signal. When the strength of the infra-red signal path by the first optical filter decreases in relation to the strength of the infra-red reference signal path by the second optical filter, this is due to water on the surface absorbing the 1900 nm wavelength more than the 2200 nm wavelength, and the electronic control causes an indicator to indicate the presence of the water.

12 Claims, 2 Drawing Sheets

METHOD AND APPARATUS TO DETECT THE PRESENCE OF WATER ON A SURFACE

BACKGROUND OF THE INVENTION

FIELD OF THE INVENTION

This invention relates to a method and apparatus to detect the presence of water on a surface.

The method and apparatus may be used to detect the presence of water on an inside surface of a fuel gas main or pipe to indicate ingress of water into the main or pipe.

SUMMARY OF THE INVENTION

According to a first aspect of the invention a method of detecting the presence of water on a surface comprises emitting an optical signal comprising at least a first wavelength and a second wavelength, both said wavelengths being absorbed by water but said first wavelength being absorbed to a greater extent than said second wavelength so that said second wavelength provides a reference, directing said optical signal onto a said surface from which the signal is reflected, alternately passing the reflected signal through a first optical filter which passes substantially only an optical signal of said first wavelength and through a second optical filter which passes substantially only an optical signal of said second wavelength, and observing when the strength of a signal emergent from the first optical filter differs in a pre-determined way from the strength of the reference passed by the second optical filter to indicate the presence of water on the surface.

According to a second aspect of the invention apparatus to detect the presence of water on a surface comprises an optical source to emit an optical signal comprising at least a first wavelength and a second wavelength, both said wavelengths being absorbed by water but said first wavelength being absorbed to a greater extent than said second wavelength so that said second wavelength provides a reference, means to direct said optical signal onto a said surface for reflection thereby, a first optical filter which passes only an optical signal of said first wavelength, a second optical filter which passes only an optical signal of said second wavelength, means to interpose alternately the first optical filter and the second optical filter in the path of the reflected optical signal, and means to observe when the strength of a signal emergent from the first optical filter differs in a predetermined way from the strength of the reference passed by the second optical filter to indicate the presence of water on the surface.

BRIEF DESCRIPTION OF THE DRAWINGS

Each aspect of the invention will now be further described, by way of example, with reference to the accompanying drawing in which.

DESCRIPTION OF THE PREFERRED EMBODIMENTS

Figure 1:
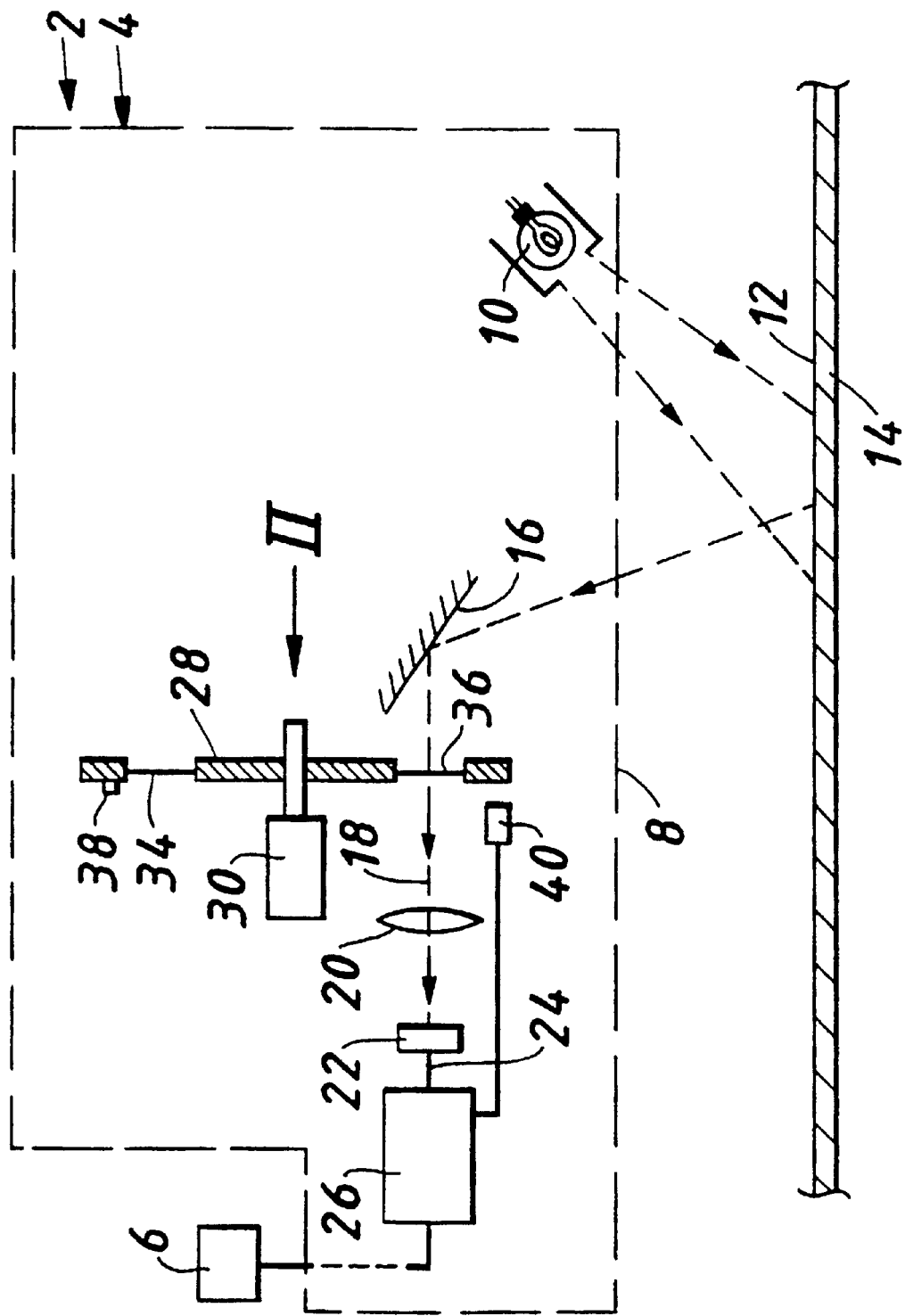
FIG. 1 is a diagrammatic representation, partly in section, of an apparatus formed according to the second aspect of the invention for carrying out the method according to the first aspect of the invention.

With reference to FIG. 1 an apparatus 2 to detect the presence of water on a surface, for example an internal surface of, for example, a pipe or main which may convey gas, for example, fuel gas, has a detection unit 4 and an indicator 6. The detection unit 4 mounted within a common casing 8, shown in dotted lines, comprises an optical source 10 to emit an optical signal in the infra-red wave band. For example, the source 10 may be a filament lamp bulb. The optical signal includes infra-red wavelengths which are absorbed by water, but some of those infra-red wave lengths are absorbed by water to a greater extent than others of those infra-red wavelengths. The arrangement is such that the emitted infra-red signal is reflected (diffusely reflected) by a surface 12, for example an inner surface of a pipe wall 14 onto a mirror or other reflector 16 so disposed that it can only receive a reflected signal and not one direct from the source 10. From reflector 16 the reflected signal follows a path 18 through a focusing lens arrangement 20 and imaged onto an infra-red detector 22, which may be a lead-sulphide type, which generates an electrical signal on line 24 representative of the strength or intensity of the infra-red signal incident on the detector 22. The signal on line 24 is input to an electronic control 26.

Figure 2:
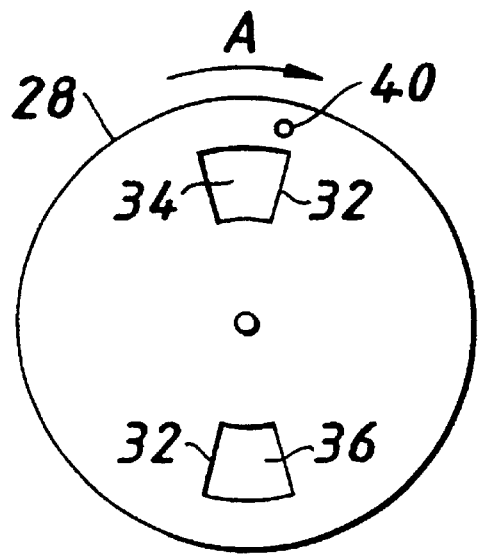
FIG. 2 is a fragmentary view of the apparatus in FIG. 1 along the arrow II.

Interposed in the reflected signal path 18 is a chopper 28 which is rotated by an electric motor 30, for example a stepper motor, and comprises, as shown in FIG. 2, a disc formed with two diametrically opposed openings or windows 32 one occupied by an optical filter 34 and the other occupied by an optical filter 36. Filter 34 only passes certain infra-red wavelengths and filter 36 only passes certain other infra-red wavelengths. All those infra-red wavelengths are absorbed by water but those passed by the filter 34 are absorbed by water to a greater extent than those passed by the filter 36. The infra-red wavelengths passed by the filter 34 have a wavelength of substantially 1900 nm, (nanometres). The signal passed by the filter 34 is hereinafter called "the water observation signal". The infra-red wavelengths passed by the filter 36 (and absorbed by water to a lesser extent than the water observation signal) serve as a reference signal. The infra-red wavelength passed by the filter 36 may be substantially 2200 nm. An infra-red signal having a wavelength of substantially 2200 nm is not absorbed by water nor by ethylene glycol (which is added to natural gas in the United Kingdom to maintain the effectiveness of gas tight seals used on fitting connected to gas mains) to the same extent as a signal of 1900 nm wavelength.

As the chopper 28 is rotated (in direction A in FIG. 2), the optical filter 34 is interposed in signal path 18 for a short time and then after a somewhat longer period the optical filter 36 is interposed in the path 18 for a time similar to that for the filter 34. The strength or intensity of the water observation signal when not absorbed by water may be substantially the same as that of the reference signal. Accordingly, when water is not present, the detector 22 responds to the water observation and reference signals substantially similarly and gives substantially the same output signal on line 24. So that control 26 can identify which signal, reference or water observation signal, is being observed by the detector 22 a marker 38 corresponding to the optical filter 34 is provided to which sensor 40 is arranged to respond. When the marker 38 passes the sensor 40 the control 26 receives a signal from that sensor indicating that the signal the control is receiving from the detector 22 corresponds to the water observing signal whereby the control 26 understands that the next signal it receives from the detector 22 corresponds to the reference signal. Thus the control 26 can distinguish between the water observation signal and the reference signal.

The control 26 observes the strength or intensity of the water observation signal and the reference signal in turn and repeatedly. The observed value of the reference signal is divided in the control 26 by the observed value of the water observation signal, and the quotient is substantially unity when water is not present. But the quotient is greater than unity when water is present to reduce the value of the detected water observation signal by absorption of at least some of that signal by the water. When the quotient exceeds the value of the water observation signal, the control 26 sends a signal to the indicator 6 to provide an indication that the presence of water is detected.

Figure 3:
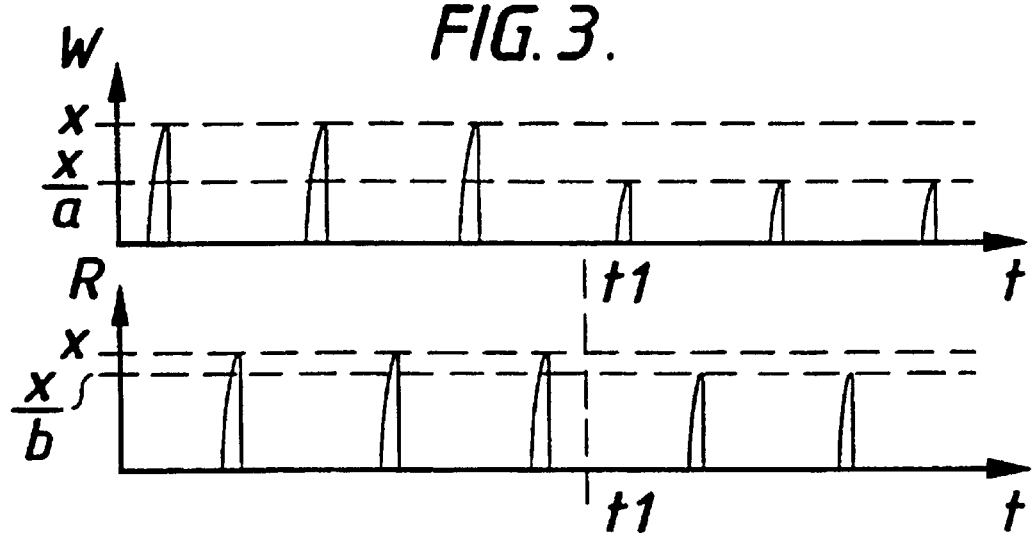
FIG. 3 is a diagrammatic representation of strengths of optical signals transmitted through the first optical filter and the second optical filter of the apparatus in FIG. 1.

FIG. 3 shows variation in the strength W of water observation signals with respect to time t received by the detector 22 and over the same time-frame variation in the strength R of signals with respect to the time t received by the detector. Initially, the values of W and R are the same, namely x so that $$\frac{x}{x} = 1$$

or unity signifying an an absence of water.

But at a time t1 and thereafter the value of W falls to $$\frac{x}{a}$$

where a is a number greater than 1, and the value of R falls to $$\frac{x}{b}$$

where b is a number less than a so that $$\frac{\frac{x}{b}}{\frac{x}{a}} = \frac{a}{b}$$

which exceeds unity signifying the presence of water.

The chopper 28 may be driven at any speed, but the faster it rotates the greater the resolution.

The use of a reference signal as a comparison means that the response of the apparatus water is not affected by variation in the reflecting properties of the surface 12 or if there is displacement of apparatus parts relative to one another, since both the reference signal and the water observation signal are each affected equally.

The apparatus 2 can be moved relative to the surface 12 to observe for the presence of water at different places on the surface.

Figure 4:
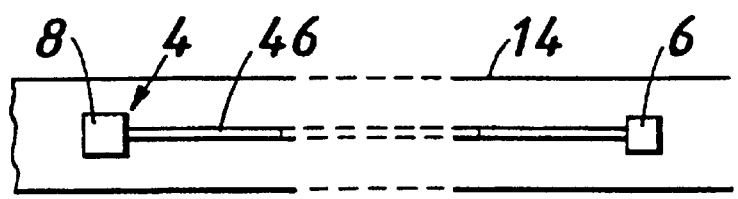
FIG. 4 is a diagrammatic representation of how the apparatus in FIG. 1 may be arranged for inspecting an interior of a pipe for the presence of water.

In FIG. 4 the detection unit 4 is shown being moved along the interior of the pipe 14 on an extensible or telescopic support or arm 46 carrying the indicator 6 at the other end.

What is claimed is:

1. A method for detecting the presence of water on an inside surface of a conduit or pipes comprising:
    emitting an optical signal comprising at least a first wavelength and a second wavelength, both said wavelengths being absorbed by water with said first wavelength being absorbed to a greater extent than said second wavelength so that said second wavelength provides a reference;
    directing said optical signal onto said inside surface of said conduit or pipe from which the signal is reflected;
    alternately passing the reflected signal through a first optical filter which passes substantially only an optical signal of said first wavelength and through a second optical filter which passes substantially only an optical signal of said second wavelength;
    observing when the strength of a signal emergent from the first optical filter differs in a pre-determined way from the strength of the reference passed by the second optical filter to indicate the presence of water on said inside surface of said conduit or pipe; and
    moving a detection unit mounted on an extensible support along the interior of said conduit or pipe to perform said emitting step at different portions of said inside surface of said conduit or pipe.

2. A method as claimed in claim 1, wherein the optical signal is an infra-red signal.

3. A method as claimed in claim 2, wherein the first optical filter substantially passes an infra-red signal having a wavelength of substantially 1900 nm.

4. A method as claimed in claim 2, wherein the second optical filter substantially only passes an infra-red signal having a wavelength of substantially 2200 nm.

5. A method as claimed in claim 1, wherein the first and second optical filter are rotated.

6. Apparatus for detecting the presence of water on an inside surface of a conduit or pipe comprising:
    a detection unit including,
        an optical source to emit an optical signal comprising at least a first wavelength and a second wavelength, both said wavelengths being absorbed by water with said first wavelength being absorbed to a greater extent than said second wavelength so that said second wavelength provides a reference,
        means for directing said optical signal onto said inside surface of said conduit or pipe for reflection thereby,
        a first optical filter which passes only an optical signal of said first wavelength,
        a second optical filter which passes only an optical signal of said second wavelength, and
        means for interposing alternately the first optical filter and the second optical filter in a path of the reflected optical signal; and
    means for observing when the strength of a signal emergent from the first optical filter differs in a pre-determined way from the strength of the reference passed by the second optical filter to indicate the presence of water on said inside surface of said conduit or pipe; and
    an extensible support to which said detection unit and said means for observing are attached.

7. An apparatus as claimed in claim 6, wherein the optical source is a source of infra-red radiation.

8. An apparatus as claimed in claim 7, wherein at least one of the first optical filter substantially only passes an infra-red signal having a wavelength of substantially 1900 nm and the second optical filter substantially only passes an infra-red signal having a wavelength of substantially 2200 nm.

9. An apparatus as claimed in claim 6, wherein the first and second optical filters are rotatable.

10. An apparatus as claimed in claim 9, wherein the first and second optical filters are mounted on a chopper.

11. An apparatus as claimed in claim 6, wherein said detection unit and said means for observing are positioned at opposite ends of said extensible support.

12. An apparatus as claimed in claim 11, wherein said extensible support is configured as a telescoping arm.

* * * * *